US005166438A

United States Patent [19]

Hashimoto et al.

[11] Patent Number: 5,166,438

[45] Date of Patent: Nov. 24, 1992

[54] 1,3-PENTADIENE DERIVATIVES AND ELECTROPHOTOGRAPHIC PHOTOCONDUCTOR USING THE SAME

[75] Inventors: Mitsuru Hashimoto, Numazu; Masaomi Sasaki, Susono; Tomoyuki Shimada, Numazu; Nobuo Suzuki, Saitama; Takayuki Sakai, Tokyo; Susumu Suzuka, Yono, all of Japan

[73] Assignees: Ricoh Company, Ltd.; Hodogaya Chemical Co., Ltd., Tokyo, Japan

[21] Appl. No.: 751,673

[22] Filed: Aug. 23, 1991

Related U.S. Application Data

[63] Continuation of Ser. No. 342,970, Apr. 25, 1989, abandoned.

[30] Foreign Application Priority Data

Apr. 26, 1988 [JP] Japan .............................. 63-101316

[51] Int. Cl.[5] .................. C07C 211/61; C07C 211/58; C07C 211/54; C07C 211/50

[52] U.S. Cl. ...................................... 564/374; 430/57; 430/58; 430/59; 430/60; 430/62; 430/67; 430/69; 544/35; 544/38; 548/444; 549/59; 564/378; 564/379; 564/384; 564/387; 564/391; 564/427; 564/428; 564/429; 564/434; 564/442; 564/443

[58] Field of Search ............... 564/373, 374, 428, 479, 564/434, 442, 443, 305, 378, 379, 384, 387, 391, 427, 429

[56] References Cited

U.S. PATENT DOCUMENTS

| | | | |
|---|---|---|---|
| 3,879,463 | 4/1975 | Peters, Jr. et al. | 260/571 |
| 4,770,973 | 9/1988 | Kanda et al. | 430/171 |
| 4,912,259 | 3/1990 | Kaneko et al. | 564/373 |

FOREIGN PATENT DOCUMENTS

| | | |
|---|---|---|
| 3810522 | 10/1988 | Fed. Rep. of Germany . |
| 2121789 | 1/1984 | United Kingdom . |

OTHER PUBLICATIONS

Hesse et al., "Distyrylcarbinols", *Chem. Abst.*, vol. 63, (1965), 11405b.

Grif et al., "Direction of nucleophilic addition, etc", Chem. Abst., vol. 92, (1980), 130592e.

*Primary Examiner*—Richard L. Raymond

*Assistant Examiner*—P. O'Sullivan

*Attorney, Agent, or Firm*—Oblon, Spivak, McClelland, Maier & Neustadt

[57] ABSTRACT

A charge transporting material comprising a 1,3-pentadiene derivative having formula (I):

$$A—CH{=}CH—CH{=}CH—CH_2—A \qquad (I)$$

wherein A represents a 9-anthryl group which may have a substituent, a N-substituted carbazolyl group which may have a substituent, a N-substituted phenothiazinyl group which may have a substituent or

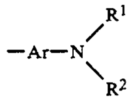

in which Ar represents an arylene group which may have a substituent, $R^1$ and $R^2$ each represent an alkyl group which may have a substituent, an aralkyl group which may have a substituent, or an aryl group which may have a substituent; an electrophotographic photoconductor comprising an electroconductive support and a photoconductive layer formed thereon, which comprises as an effective component at least one of the 1,3-pentadiene derivatives of the above formula (I); and novel 1,3-pentadiene derivatives of the formula (I), provided that in the formula (I), $R^1$ and $R^2$ cannot be a methyl group at the same time, are disclosed.

4 Claims, 2 Drawing Sheets

1,3-PENTADIENE DERIVATIVES AND ELECTROPHOTOGRAPHIC PHOTOCONDUCTOR USING THE SAME

This application is a continuation of application Ser. No. 07/342,970 filed on Apr. 25, 1989, now abandoned.

BACKGROUND OF THE INVENTION

1. Field of the Invention

The present invention relates to 1,3-pentadiene derivatives and an electrophotographic photoconductor which comprises a photoconductive layer comprising at least one of the 1,3-pentadiene derivatives.

2. Discussion of Background

Some examples of photoconductive materials for use in the conventional photoconductors used in electrophotography include inorganic materials such as selenium, cadmium sulfide and zinc oxide. In an electrophotographic process, a photoconductor is first exposed to corona discharge in the dark, so that the surface of the photoconductor is electrically charged in a uniform manner. The thus uniformly charged photoconductor is then exposed to original light images and the exposed portions selectively become electroconductive, causing the dissipation of electric charges from these portions of the photoconductor. Latent electrostatic images, corresponding to the original light images, are thus formed on the surface of the photoconductor. The latent electrostatic images are then developed by a so-called "toner" which comprises a colorant, such as a dye or a pigment, and a binder agent made of a polymeric material. Through this process, visible, developed images can be obtained on the photoconductor.

The fundamental requirements of a photoconductor for use in electrophotography are: (1) chargeability to a predetermined potential in the dark; (2) minimal electric charge dissipation in the dark; and (3) rapid dissipation of electric charges upon exposure to light.

While the above-mentioned inorganic photoconductive materials have many advantages over other conventional photoconductive materials, they also have several drawbacks. For example, the selenium photoconductor, which is widely used at present and sufficiently meets the above-mentioned requirements (1) to (3), is also characterized by difficult methods which ultimately result in increased production costs. The properties of the material itself are less than desirable. Its low flexibility hinders the process of forming it into a belt. As well, its vulnerability to thermal and mechanical shocks necessitates extremely careful material handling.

Cadmium sulfide photoconductors and zinc oxide photoconductors are prepared by dispersing cadmium sulfide or zinc oxide in a binder resin. Due to this dispersive condition, the mechanical properties of the resulting material are poor such as surface smoothness, hardness, tensile strength and wear resistance. Thus these materials are not suitable for use as photoconductors where much repetition is encountered, such as in plain paper copiers.

Recently, varieties of organic electrophotographic photoconductors have been proposed to cover the shortcomings of the inorganic photoconductor. Some of them are now being used in practice. Representative examples of the organic electrophotographic photoconductor include one that is comprised of poly-N-vinylcarbazole and 2,4,7-trinitrofluorene-9-on U.S. Pat. No. 3,484,237), a photoconductor in which poly-N-vinylcarbazole is sensitized by a pyrylium salt type dyestuff (Japanese Patent Publication 48-25658), a photoconductor containing a main component of organic pigment (Japanese Laid-Open Patent Application 47-37543), and a photoconductor containing as the main component, an eutectic crystalline complex made of a dye and a resin (Japanese Laid-Open Patent Application 47-10735).

Although the above-mentioned organic electrophotographic photoconductors have many superior in many respects to other conventional photoconductors, they do not satisfy all the requirements of an electrophotographic photoconductor.

SUMMARY OF THE INVENTION

It is therefore a first object of the present invention to provide novel 1,3-pentadiene derivatives, which may be employed in electrophotographic photoconductors.

A second object of the present invention is to provide an electrophotographic photoconductor from which the previously mentioned conventional shortcomings are eliminated, and which can meet all the requirements of an electrophotographic photoconductor in terms of the fundamental electrophotographic characteristics.

A third object of the present invention is to provide an electrophotographic photoconductor which has high flexibility and durability and can be easily manufactured at a low cost.

The first object of the present invention can be achieved by 1,3-pentadiene derivatives having the following formula (I):

$$A—CH=CH—CH=CH—CH_2—A \qquad (I)$$

wherein A represents a 9-anthryl group which may have a substituent, a N-substituted carbazolyl group which may have a substitutent, a N-substituted phenothiazinyl group which may have a substituent or

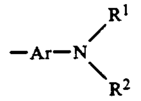

in which Ar represents an arylene group which may have a substituent, $R^1$ and $R^2$ each represent (i) an alkyl group which may have a substituent, provided that $R^1$ and $R^2$ cannot be a methyl group at the same time, (ii) an aralkyl group which may have a substituent, or (iii) an aryl group which may have a substituent.

The second and third objects of the present invention can be attained by an electrophotographic photoconductor comprising an electroconductive support and a photoconductive layer formed thereon, which comprises as an effective component at least one of 1,3-pentadiene derivatives of the above formula (I), in which $R^1$ and $R^2$ may be a methyl group at the same time.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
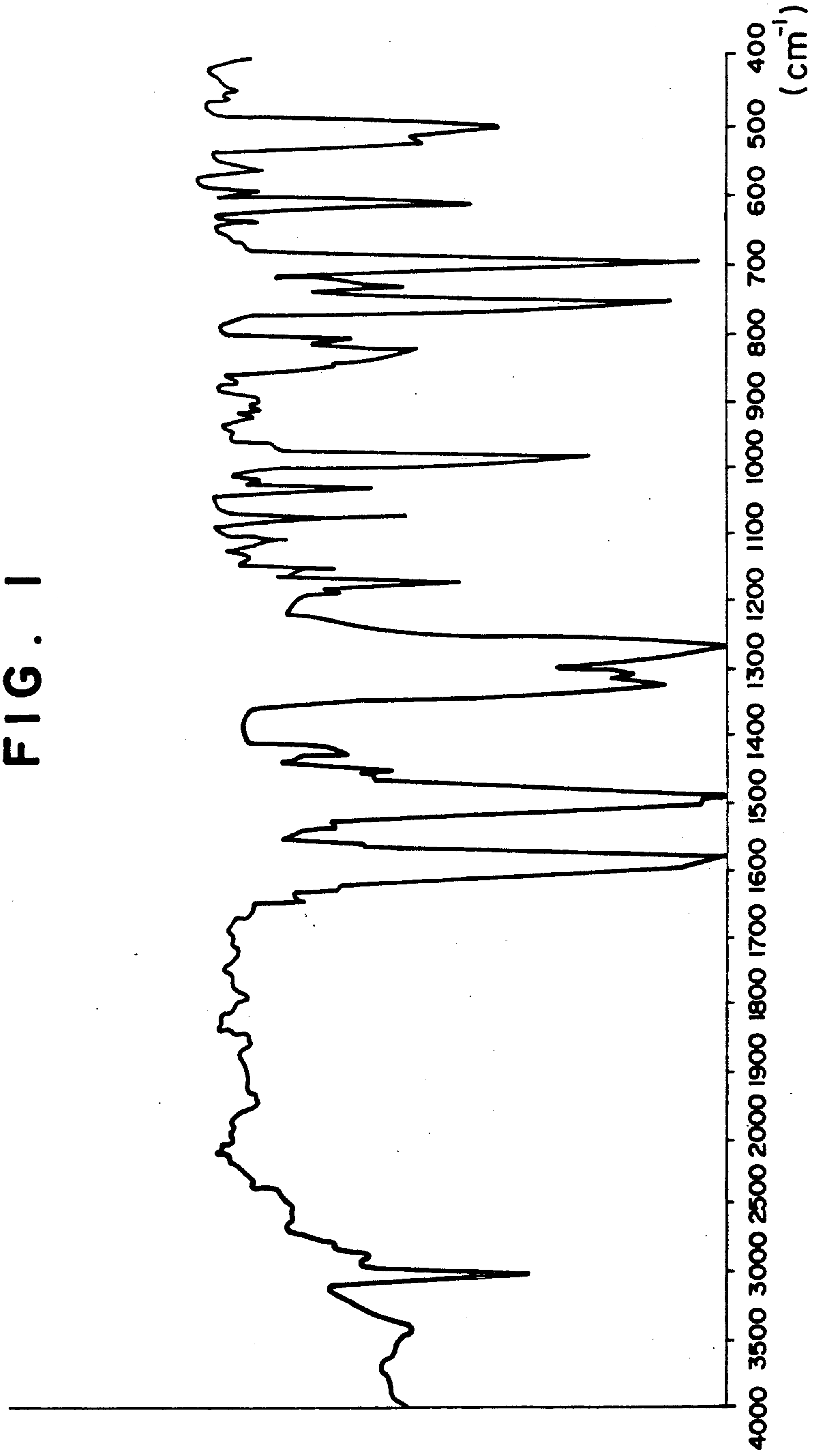
FIG. 1 is an infrared spectra of 1,3-pentadiene derivative obtained in Synthesis Example 1.

As mentioned previously, the 1,3-pentadiene derivatives according to the present invention have the following formula (I):

$$A—CH=CH—CH=CH—CH_2—A \quad (I)$$

wherein A represents a 9-anthryl group which may have a substituent, a N-substituted carbazolyl group which may have a substituent, a N-substituted phenothiazinyl group or

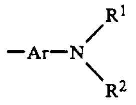

in which Ar represents an arylene group which may have a substituent, $R^1$ and $R^2$ each represent an alkyl group which may have a substituent,, provided that $R^1$ and $R^2$ cannot be a methyl group at the same time, an aralkyl group which may have a substituent, an aralkyl group which may have a substituent, or an aryl group which may have a substituent.

In the above formula (I), an example of the substituent of the 9-anthryl group is a halogen such as bromine; examples of the substituent of the N-substituted carbazolyl group include an alkyl group having 1 to 4 carbon atoms which may have a substituent such as a halogen and a hydroxyl group, and a phenyl group which may have a substituent such as an alkyl group having 1 to 4 carbon atoms and an alkoxyl group having 1 to 4 carbon atoms; examples of the substituent of the N-substituted phenothiazinyl group include an alkyl group having 1 to 4 carbon atoms; examples of the substituent of the arylene group represented by Ar include an alkyl group having 1 to 4 carbon atoms, and an alkoxyl group having 1 to 4 carbon atoms; examples of the alkyl group represented by $R^1$ or $R^2$ include an alkyl group having 1 to 4 carbon atoms, which may have a substituent such as an unsubstituted or substituted phenyl group; examples of the substituent of the aralkyl group or aryl group represented by $R^1$ or $R^2$ include an alkyl group having 1 to 4 carbon atoms, an alkoxyl group having 1 to 4 carbon atoms, a halogen such as chlorine, and a phenyl group.

The 1,3-pentadiene derivatives having the formula (I) according to the present invention can be prepared by allowing a 1,3-propylene derivative, represented by the following formula (II), to react with an aldehyde compound, represented by the formula (III), preferably in the presence of a basic catalyst.

$$Y-(CH_2)_3-Y \quad (II)$$

wherein Y represents

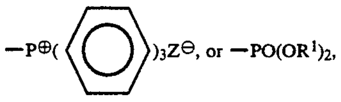

in which $Z^\ominus$ represents a halogen ion; and $R^1$ represents a lower alkyl group.

$$A—CHO \quad (III)$$

wherein A represents a 9-anthryl group which may have a substituent, a N-substituted carbazolyl group which may have a substituent, a N-substituted phenothiazinyl group or

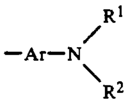

in which Ar represents an arylene group which may have a substituent, $R^1$ and $R^2$ each represent an alkyl group which may have a substituent, an aralkyl group which may have a substituent, or an aryl group which may have a substituent.

Specific examples of the basic catalyst for the above reaction include potassium hydroxide, sodium amide, sodium methylate, potassium methylate and alcoholates such as potassium t-butoxide.

Specific examples of the reaction solvent are methanol, ethanol, propanol, toluene, xylene, dioxane, N,N-dimethylformamide, dimethyl sulfoxide, and tetrahydrofuran.

The temperature for the above reaction can be set in a relatively wide range. This range depends on (1) the stability of the solvent employed in the presence of the basic catalyst, (2) the reactivities of the condensation components, (that is, the compounds of the formulas (II) and (III)), and (3) the reactivity of the basic catalyst in the solvent employed, which works as a condensation agent in this reaction.

When a polar solvent is, for example, employed as the reaction solvent, the reaction temperature can be set in the range of room temperature to about 100° C., preferably in the range of room temperature to about 80° C. However, if a shorter reaction time is desired or a less reactive condensation agent is employed, the reaction temperature can be elevated beyond this range.

The above-mentioned 1,3-propylene derivatives of the formula (II) which serves as a starting material for the production of the 1,3-pentadiene derivatives according to the present invention can be easily produced. For example, one method is to allow a 1,3-dihalogenopropylene compound to directly react with trialkyl phosphite or triphenylphosphine under the application of heat. Alternatively, the above-mentioned reaction may be carried out in an organic solvent such as toluene, xylene or dimethylformamide.

As previously mentioned, the electrophotographic photoconductor according to the present invention comprises a photoconductive layer comprising as an effective component at least one of 1,3-pentadiene derivatives represented by the formula I) in which $R^1$ and $R^2$ may be a methyl group and the same time.

These 1,3-pentadiene derivatives can either be optically or chemically sensitized by sensitizers such as dyes and Lewis acids. Furthermore, the above-mentioned 1,3-pentadiene derivatives are particularly useful as charge transporting materials employed in the function-separating type photoconductor which uses an organic or inorganic pigment as a charge generating material.

Specific examples of the above-mentioned 1,3-pentadiene derivatives for use in the electrophotographic photoconductor according to the present invention are as follows:

TABLE 1

[$A-CH=CH-CH=CH-CH_2-A$]

| 1,3-pentadien derivative No. | A |
|---|---|
| 1 | 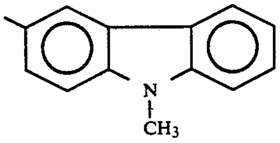 |
| 2 | 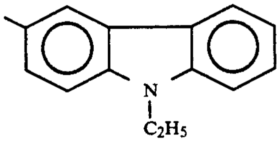 |
| 3 | 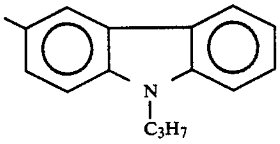 |
| 4 | 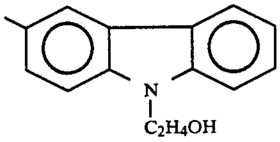 |
| 5 | 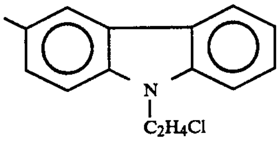 |
| 6 | 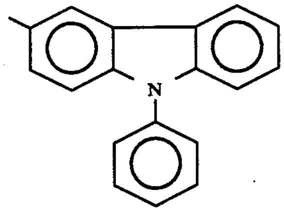 |
| 7 | 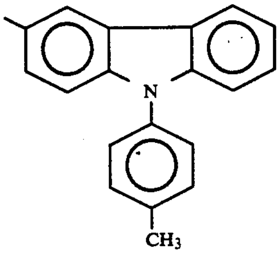 |

TABLE 1-continued
| | |
|---|---|
| 8 | 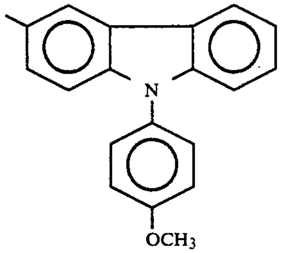 |
| 9 | 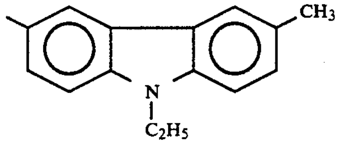 |
| 10 | 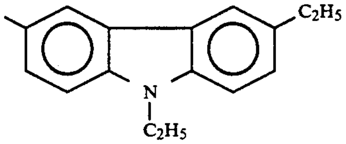 |
| 11 | 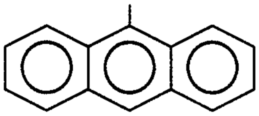 |
| 12 | 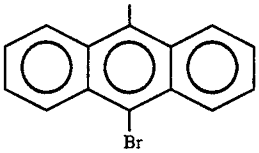 |
| 13 | 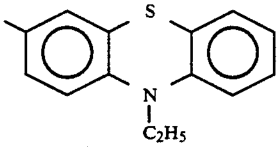 |
$A—CH=CH—CH=CH—CH_2—A$ in which A = 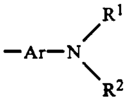
| 1,3-pentadien derivative No. | Ar | $R^1$ | $R^2$ |
|---|---|---|---|
| 14 | 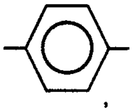 | $—CH_3$ | $—CH_3$ |
| 15 | 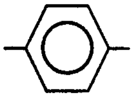 | $—C_2H_5$ | $—C_2H_5$ |
| 16 | 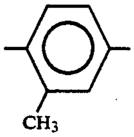 | $—C_2H_5$ | $—C_2H_5$ |

TABLE 1-continued
| | | | |
|---|---|---|---|
| 17 | 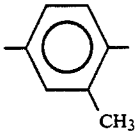 | $-C_2H_5$ | $-C_2H_5$ |
| 18 | 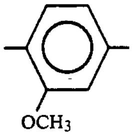 | $-C_2H_5$ | $-C_2H_5$ |
| 19 | 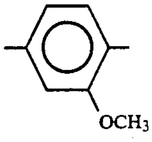 | $-C_2H_5$ | $-C_2H_5$ |
| 20 | 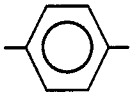 | $-CH_3$ | 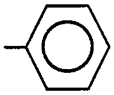 |
| 21 | 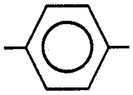 | $-C_2H_5$ | 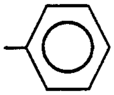 |
| 22 | 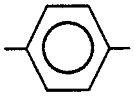 | 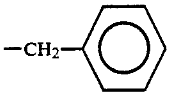 | 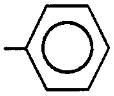 |
| 23 | 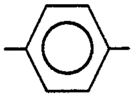 | 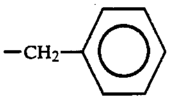 | 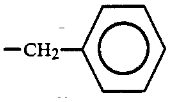 |
| 24 | 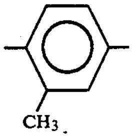 | 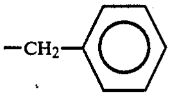 | 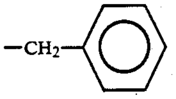 |
| 25 | 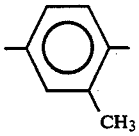 | 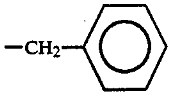 | 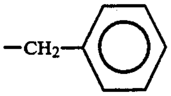 |
| 26 | 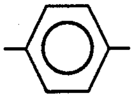 | 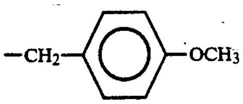 | 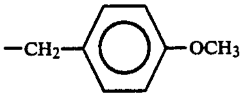 |
| 27 | 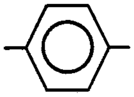 | 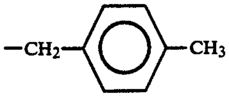 | 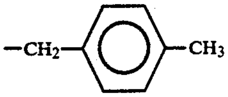 |
| 28 | 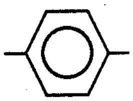 | 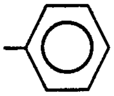 | 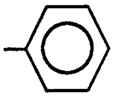 |

TABLE 1-continued
| | |
|---|---|
| 29 | 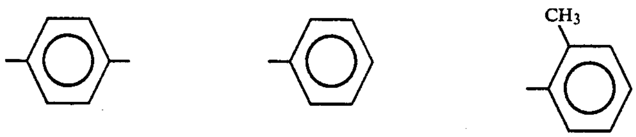 |
| 30 | 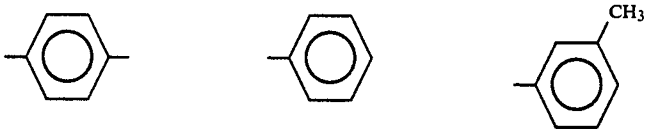 |
| 31 | 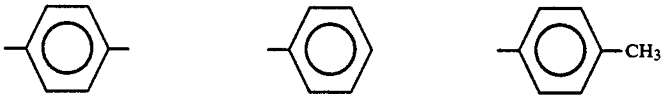 |
| 32 | 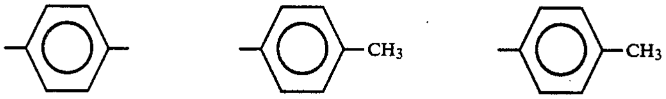 |
| 33 | 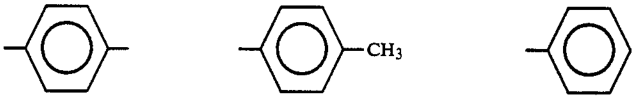 |
| 34 | 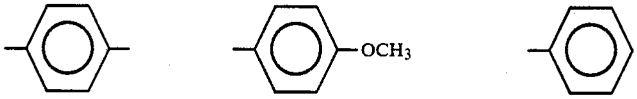 |
| 35 | 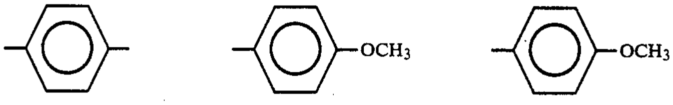 |
| 36 | 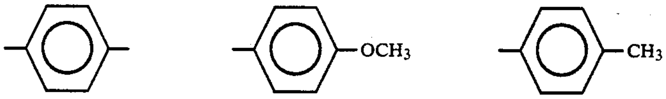 |
| 37 | 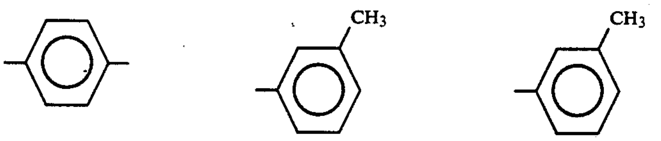 |
| 38 | 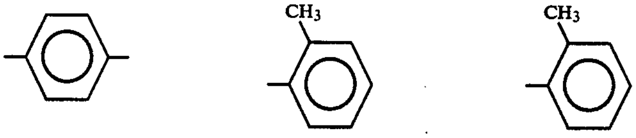 |
| 39 | 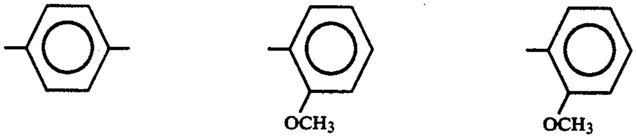 |
| 40 | 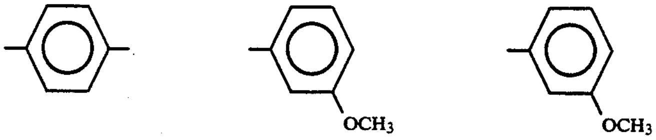 |

TABLE 1-continued
| | | | |
|---|---|---|---|
| 41 | 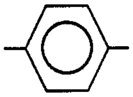 | 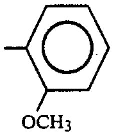 | 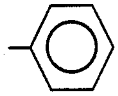 |
| 42 | 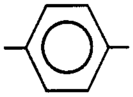 | 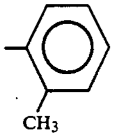 | 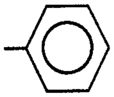 |
| 43 | 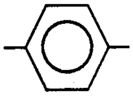 | 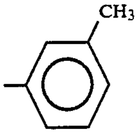 | 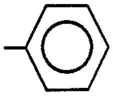 |
| 44 | 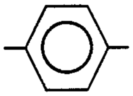 | 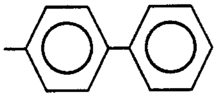 | 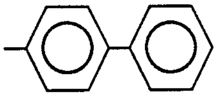 |
| 45 | 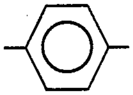 | 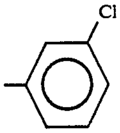 | 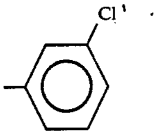 |
| 46 | 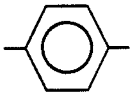 | 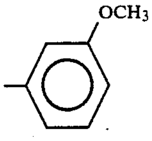 | 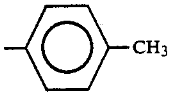 |
| 47 | 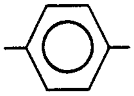 | 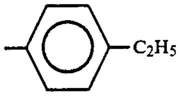 | 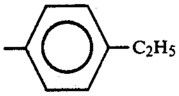 |
| 48 | 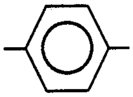 | 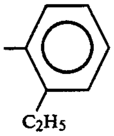 | 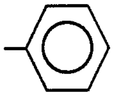 |
| 49 | 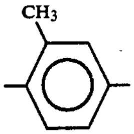 | 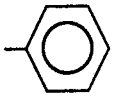 | 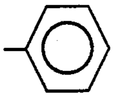 |
| 50 | 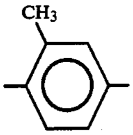 | 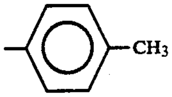 | 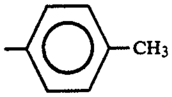 |
| 51 | 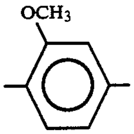 | 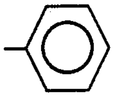 | 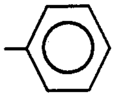 |

TABLE 1-continued
| | | | |
|---|---|---|---|
| 52 | 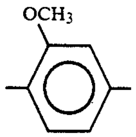 | 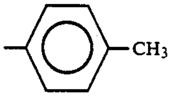 | 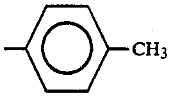 |
| 53 | 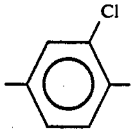 | 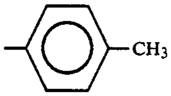 | 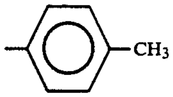 |
| 54 | 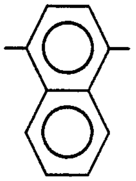 | 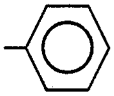 | 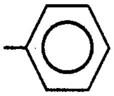 |
| 55 | 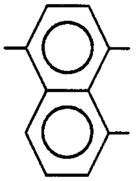 | 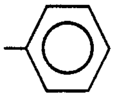 | 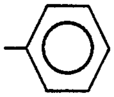 |
| 56 | 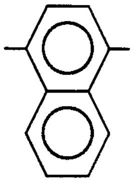 | 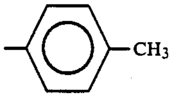 | 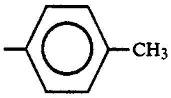 |
| 57 | 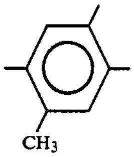 | 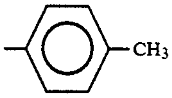 | 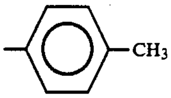 |
| 58 | 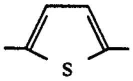 | 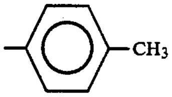 | 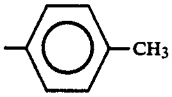 |
| 59 | 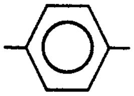 | 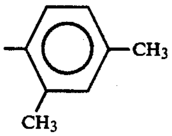 | 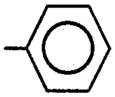 |
| 60 | 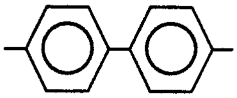 | 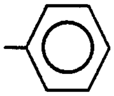 | 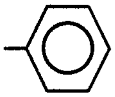 |
| 61 | 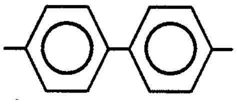 | 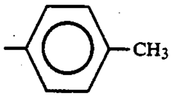 | 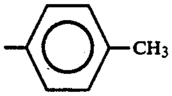 |

TABLE 1-continued

| | | | |
|---|---|---|---|
| 62 | 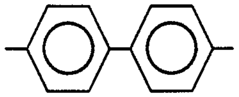 | 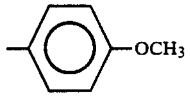 | 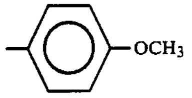 |

The present invention will now be explained in detail by referring to the following synthesis examples of the 1,3-pentadiene derivatives.

SYNTHESIS EXAMPLE 1

Synthesis of 1,3-pentadiene Derivative No. 28 in Table 1

A mixture of 55.0 g (0.075 mole) of trimethylene-1,3-bis(triphenylphosphonium)dibromide and 41.4 g (0.15 mole) of 4-N,N-diphenylaminobenzaldehyde was dissolved in 300 ml of toluene. To this solution, 15.4 g (0.22 mole) of finely-divided particles of potassium methylate was gradually added at 10° C. or below. After the completion of the dropwise addition of finely-divided particles of potassium methylate, the solution was stirred in a stream of a nitrogen gas, with the temperature maintained at 15° C. to 18° C. for 4 hours. The obtained reaction mixture was diluted with 120 ml of water and the reaction product was extracted with toluene. The toluene was partially removed from the extract solution to obtain an extract. This extract was subjected to chromatography using silica gel as a carrier and n-hexane/toluene as an eluting solution. This extract was then recrystallized from a mixed solvent of toluene and n-hexane, whereby 15.8 g of 1,5-bis(4-N,N-diphenylaminophenyl)-1,3-pentadiene, which is given as 1,3-pentadiene derivative No. 28 according to the present invention in Table 1, was obtained in the form of white crystals in a 38% yield. The melting point of the product was at 104.5° C. to 105.5° C.

The results of the elemental analysis of the thus obtained 1,3-pentadiene derivative No. 28 were as follows:

| | % C | % H | % N |
|---|---|---|---|
| Calculated | 88.77 | 6.18 | 5.50 |
| Found | 88.76 | 6.10 | 5.43 |

The above calculation was based on the formula for 1,3-pentadiene derivative No. 28 of $C_{41}H_{34}N_2$.

An infrared absorption spectrum of the above 1,3-pentadiene derivative No. 28, taken using a KBr tablet, is shown in FIG. 1.

SYNTHESIS EXAMPLES 2to 9

Synthesis Example 1 was repeated except that the 4-N,N-diphenylaminobenzaldehyde employed in Synthesis Example 1 was replaced by aldehyde compounds No. 2 to No. 9 as shown in Table 2. Thus, the 1,3-pentadiene derivatives of the present invention were obtained.

The melting points and the results of the elemental analysis of the obtained 1,3-pentadiene derivatives are also shown in Table 2.

TABLE 2

| Synthesis Example No. | Aldehyde Compound | 1,3-pentadiene Derivative | Melting Point (°C.) (Solvent for Recrystal-lization | Elemental Analysis Found (%)/Calculated (%) C | H | N |
|---|---|---|---|---|---|---|
| 2 | 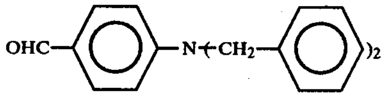 | 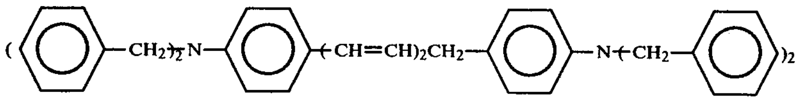 (1,3-pentadiene derivative No. 23 in Table 1) | 117–118 (Toluene/ n-hexane) | 88.35/88.48 | 6.89/6.93 | 4.62/4.59 |
| 3 | 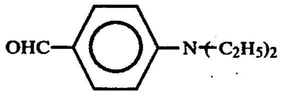 | 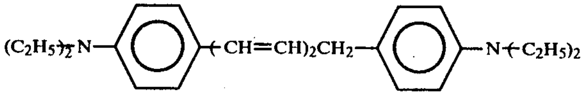 (1,3-pentadiene derivative No. 15 in Table 1) | Oily | 82.78/82.82 | 9.40/9.45 | 7.62/7.73 |
| 4 | 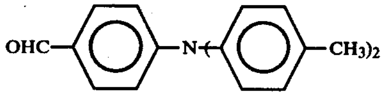 | 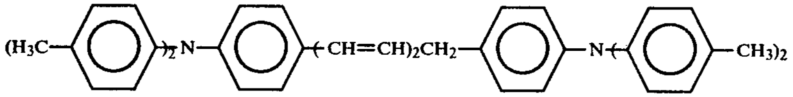 (1,3-pentadiene derivative No. 23 in Table 1) | 73–75 (Toluene/ n-hexane) | 88.50/88.48 | 6.93/6.93 | 4.55/4.59 |
| 5 | 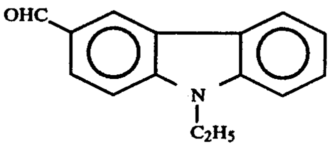 | 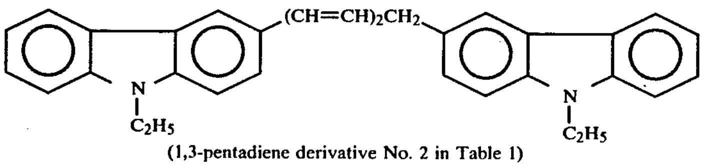 (1,3-pentadiene derivative No. 2 in Table 1) | 151.5–152 (Toluene/ n-hexane) | 86.97/87.18 | 6.33/6.65 | 6.20/6.16 |
| 6 | 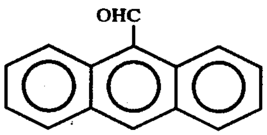 | 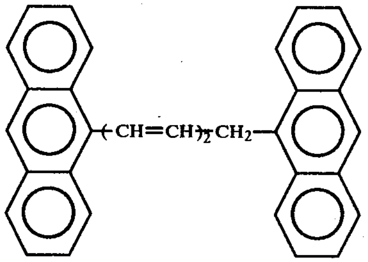 (1,3-pentadiene derivative No. 11 in Table 1) | 186.0–187.0 (Toluene/ n-hexane) | 94.17/94.25 | 5.73/5.75 | — |

TABLE 2-continued
| Synthesis Example No. | Aldehyde Compound | 1,3-pentadiene Derivative | Melting Point (°C.) (Solvent for Recrystallization | Elemental Analysis Found (%)/Calculated (%) C | H | N |
|---|---|---|---|---|---|---|
| 7 | 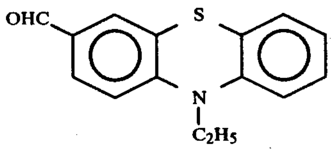 | 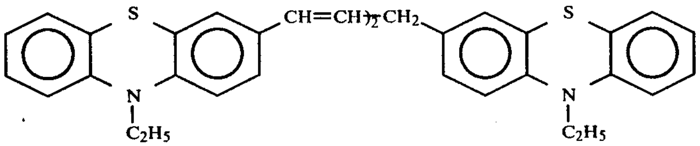 (1,3-pentadiene derivative No. 13 in Table 1) | 74.0-76.0 (Toluene/n-hexane) | 76.40/76.41 | 5.85/5.83 | 5.28/5.40 |
| 8 | 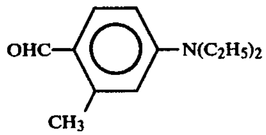 | 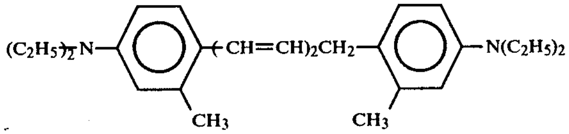 (1,3-pentadiene derivative No. 16 in Table 1) | Oily | 82.97/83.02 | 9.80/9.81 | 7.12/7.12 |
| 9 | 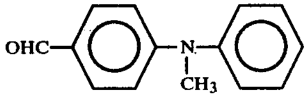 | 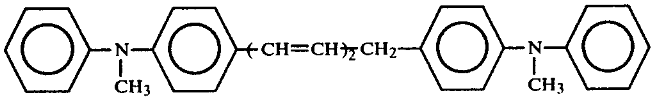 (1,3-pentadiene derivative No. 20 in Table 1) | 89-91 (n-hexane) | 86.42/86.47 | 7.00/7.02 | 6.49/6.51 |

In the photoconductors according to the present invention, at least one of the 1,3-pentadiene derivatives of the formula (I), in which $R^1$ and $R^2$ may be a methyl group at the same time, is contained in the photoconductive layers 2a, 2b, 2c, 2d and 2e as shown in FIGS. 2 to 6. The 1,3-pentadiene derivatives can be employed in different ways, for example, as shown in these figures.

Figure 2:
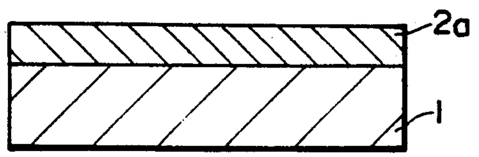
FIG. 2 is a schematic cross-sectional view of a first embodiment of an electrophotographic photoconductor according to the present invention.

In the photoconductor as shown in FIG. 2, a photoconductive layer 2a is formed on an electroconductive support 1, which photoconductive layer 2a comprises a 1,3-pentadiene derivative, a sensitizer dye and a binder agent. In this photoconductor, the 1,3-pentadiene derivative works as a photoconductive material, through which charge carriers which are necessary for the light decay of the photoconductor are generated and transported. However, the 1,3-pentadiene derivative itself scarcely absorbs light in the visible light range and, therefore, it is necessary to add a sensitizer dye which absorbs light in the visible light range in order to form latent electrostatic images by us of visible light.

Figure 3:
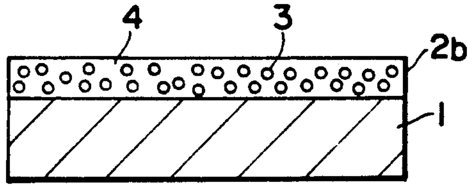
FIG. 3 is a schematic cross-sectional view of a second embodiment of an electrophotographic photoconductor according to the present invention.

Referring to FIG. 3, there is shown an enlarged cross-sectional view of another embodiment of an electrophotographic photoconductor according to the present invention. In the figure, reference numeral 1 indicates an electroconductive support. On the electroconductive support 1, there is formed a photoconductive layer 2b comprising a charge generating material 3 dispersed in a charge transporting medium 4 comprising a 1,3-pentadiene derivative and a binder agent. In this embodiment, the 1,3-pentadiene derivative works as a charge transporting material; and the 1,3-pentadiene derivative and the binder agent in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the 1,3-pentadiene derivative not overlap in the visible light range. This is because, in order that the charge generating material 3 produce charge carriers efficiently, it is necessary that light pass through the charge transporting medium 4 and reach the surface of the charge generating material 3. Since the 1,3-pentadiene derivatives of the previously described general formula (I) do not substantially absorb light in the visible range, they can work effectively as charge transporting materials in combination with the charge generating material 3 which absorbs the light in the visible region and generates charge carriers.

Figure 4:
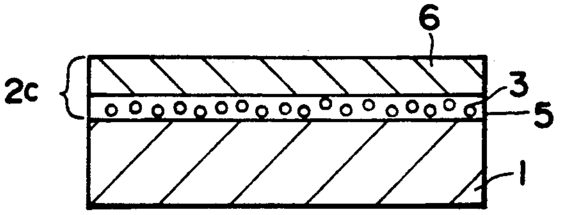
FIG. 4 is a schematic cross-sectional view of a third embodiment of an electrophotographic photoconductor according to the present invention.

Referring to FIG. 4, there is shown an enlarged cross-sectional view of a further embodiment of an electrophotographic photoconductor according to the present invention. In the figure, there is formed on the electroconductive support 1 a two-layered photoconductive layer 2c comprising a charge generation layer 5 containing the charge generating material 3, and a charge transport layer 6 containing a 1,3-pentadiene derivative of the previously described formula (I).

In this photoconductor, light which has passed through the charge transport layer 6 reaches the charge generation layer 5 and charge carriers are generated within the charge generation layer 5. The charge carriers which are necessary for the light decay for latent electrostatic image formation are generated by the charge generating material 3, accepted and transported by the charge transport layer 6. In the charge transport layer 6, the 1,3-pentadiene derivative mainly works for transporting charge carriers. The generation and transportation of the charge carriers are performed by the same mechanism as that in the photoconductor shown in FIG. 3.

Figure 5:
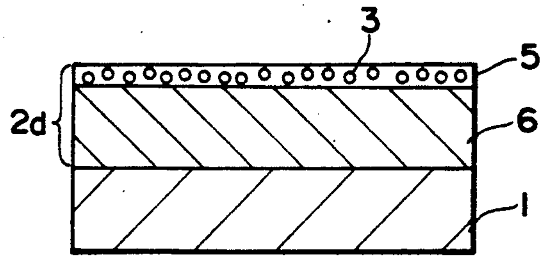
FIG. 5 is a schematic cross-sectional view of a fourth embodiment of an electrophotographic photoconductor according to the present invention.

The electrophotographic photoconductor shown in FIG. 5, the charge generation layer 5 is formed on the charge transport layer 6 containing the 1,3-pentadiene derivative in the photoconductive layer 2d, thus the overlaying order of the charge generation layer 5 and the charge transport layer 6 is reversed as compared with the electrophotographic photoconductor as shown in FIG. 4. The mechanism of the generation and transportation of charge carriers is substantially the same as that of the photoconductor shown in FIG. 4.

Figure 6:
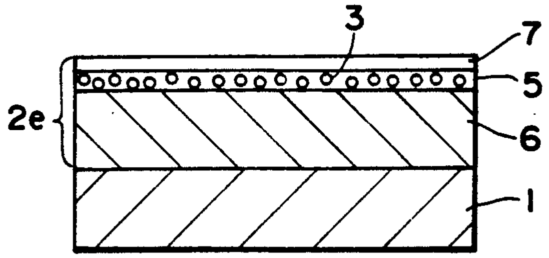
FIG. 6 is a schematic cross-sectional view of a fifth embodiment of an electrophotographic photoconductor according to the present invention.

In the above photoconductor, a protective layer 7 may be formed on the charge generation layer 5 as shown in FIG. 6 for protecting the charge generation layer 5.

When the electrophotographic photoconductor according to the present invention as shown in FIG. 2 is prepared, at least one 1,3-pentadiene derivative of the previously described formula (I) is dispersed in a binder resin solution, and a sensitizer dye is then added to the mixture, so that a photoconductive layer coating liquid is prepared. The thus prepared photoconductive layer coating liquid is coated on an electroconductive support 1 and dried, so that a photoconductive layer 2a is formed on the electroconductive support 1.

It is preferable that the thickness of the photoconductive layer 2a be in the range of 3 μm to 50 μm, more preferably in the range of 5 μm to 20 μm. It is preferable that the amount of the 1,3-pentadiene derivative contained in the photoconductive layer 2a be in the range of 30 wt. % to 70 wt. %, more preferably about 50 wt. % of the total weight of the photoconductive layer 2a. Further, it is preferable that the amount of the sensitizer dye contained in the photoconductive layer 2a be in the range of 0.1 wt. % to 5 wt. %, more preferably in the range of 0.5 wt. % to 3 wt. %, of the total weight of the photoconductive layer 2a.

As the sensitizer dye, the following can be employed in the present invention: Triarylmethane dyes, such as Brilliant Green, Victoria Blue B, Methyl Violet, Crystal Violet, and Acid Violet 6B; xanthene dyes, such as Rhodamine B, Rhodamine 6G, Rhodamine G Extra, Eosin S, Erythrosin, Rose Bengale, and Fluorescein; thiazine dyes, such as Methylene Blue; cyanin dyes, such as cyanin; and pyrylium dyes, such as 2,6-diphenyl-4-(N,N-dimethylaminophenyl) thiapyrylium perchlorate and benzopyrylium salt (Japanese Patent Publication 48-25658). These sensitizer dyes can be used alone or in combination.

An electrophotographic photoconductor according to the present invention as shown in FIG. 3 can be prepared, for example, as follows. A charge generating material in the form of small particles is dispersed in a solution of one or more 1,3-pentadiene derivatives and a binder agent. The thus prepared dispersion is coated on the electroconductive support 1 and then dried, whereby a photoconductive layer 2b is formed on the electroconductive support 1.

It is preferable that the thickness of the photoconductive layer 2b be in the range of 3 μm to 50 μm, more preferably in the range of 5 μm to 20 μm. It is preferable that the amount of the 1,3-pentadiene derivative contained in the photoconductive layer 2*b* be in the range of 10 wt. % to 95 wt. %, more preferably in the range of 30 wt. % to 90 wt. %, of the total weight of the photoconductive layer 2*b*. Further, it is preferable that the amount of the charge generating material 3 contained in the photoconductive layer 2*b* be in the range of 0.1 wt. % to 50 wt. %, more preferably in the range of 1 wt. % to 20 wt. %, of the total weight of the photoconductive layer 2*b*.

As the charge generating material 3, the following can be employed in the present invention: Inorganic pigments, such as selenium, a selenium-tellurium alloy, cadmium sulfide, a cadmium sulfide - selenium alloy and α-silicon; and organic pigments, for example, C.I. Pigment Blue 25 (C.I. 21180), C.I. Pigment Red 41 (C.I. 21200), C.I. Acid Red 52 (C.I. 45100), and C.I. Basic Red 3 (C.I. 45210); azo pigments having a carbazole skeleton (Japanese Laid-Open Patent Application 53-95033), azo pigments having a distyrylbenzene skeleton (Japanese Laid-Open Patent Application 53-133445), azo pigments having a triphenylamine skeleton (Japanese Laid-Open Patent Application 53-132347), azo pigments having a dibenzothiophene skeleton (Japanese Laid-Open Patent Application 54-21728), azo pigments having an oxadiazole skeleton (Japanese Laid-Open Patent Application 54-12742), azo pigments having a fluorenone skeleton (Japanese Laid-Open Patent Application 54-22834), azo pigments having a bisstilbene skeleton (Japanese Laid-Open Patent Application 54-17733), azo pigments having a distyryl oxadiazole skeleton (Japanese Laid-Open Patent Application 54-2129), azo pigments having a distyryl carbazole skeleton (Japanese Laid-Open Patent Application 54-14967); phthalocyanine-type pigments such as C.I. Pigment Blue 16 (C.I. 74100); Indigo-type pigments such as C.I. Vat Brown 5 (C.I. 73410) and C.I. Vat Dye (C.I. 73030); and perylene-type pigments, such as Algo Scarlet B (made by Bayer Co., Ltd.) and Indanthrene Scarlet R (made by Bayer Co., Ltd). These charge generating materials can be used alone or in combination.

An electrophotographic photoconductor according to the present invention as shown in FIG. 4 can be prepared, for example, as follows. A charge generating material 3 is vacuum-evaporated on the electroconductive support 1, whereby a charge generation layer 5 is formed. Alternatively, a charge generating material 3 in the form of fine particles is dispersed in a solution of a binder agent, and this dispersion is applied to the electroconductive support material 1 and then dried, and, if necessary, the applied layer is subjected to buffing to make the surface smooth or to adjust the thickness of the layer to a predetermined thickness, whereby a charge generation layer 5 is formed. A charge transport layer 6 is then formed on the charge generation layer 5 by applying a solution of one or more 1,3-pentadiene derivatives and a binder agent to the charge generation layer 5 and then drying the applied solution. In this photoconductor, the charge generating material employed is the same as that employed in the photoconductor in FIG. 3.

It is preferable that the thickness of the charge generation layer 5 be 5 μm or less, more preferably 2 μm or less. It is preferable that the thickness of the charge transport layer 6 be in the range of 3 μm to 50 μm, more preferably in the range of 5 μm to 20 μm. In the case where the charge generation layer 5 comprises a charge generating material in the form of fine particles, dispersed in a binder agent, it is preferable that the amount of the charge generating material in the charge generation layer 5 be in the range of 10 wt. % to 95 wt. %, more preferably in the range of about 50 wt. % to about 90 wt. % of the entire weight of the charge generation layer 5. Further, it is preferable that the amount of the 1,3-pentadiene derivative contained in the charge transport layer 6 be in the range of 10 wt. % to 95 wt. %, more preferably in the range of 30 wt. % to 90 wt. %, of the total weight of the charge transport layer 6.

The electrophotographic photoconductor as shown in FIG. 5 can be prepared, for example, by coating a solution of the 1,3-pentadiene derivative and a binder agent on the electroconductive support 1 and drying the same to form a charge transport layer 6, and then coating on the charge transport layer 6 a dispersion of finely-divided charge generating material, with addition thereto of a binder agent when necessary, by spray coating, and drying the coated dispersion to form a charge generation layer 5 on the charge transport layer 6. The thickness of each of the two layers 5 and 6 and the compositions thereof may be the same as those of the photoconductive layer 2*c* in the photoconductor shown in FIG. 4.

When a protective layer 7 is formed on the charge generation layer 5 of the photoconductive layer 2*e* by coating an appropriate resin solution, for instance, by spray coating, the photoconductor as shown in FIG. 6 can be prepared.

As the electroconductive support 1 for use in the present invention, a metal plate or metal foil, for example, made of aluminum, a plastic film on which a metal, for example, aluminum, is evaporated, or paper which has been treated so as to be electroconductive, can be employed.

As the binder agent for use in the present invention, condensation resins, such as polyamide, polyurethane polyester, epoxy resin, polyketone and polycarbonate; and vinyl polymers such as polyvinylketone, polystyrene, poly-N-vinylcarbazole and polyacrylamide, can be used. These resins can also be employed as a resin component in the above mentioned protective layer 7.

Other conventional electrically insulating and adhesive resins can also be used as the binder agent in the present invention. When necessary, there can be added to the binder resins a plasticizer, for example, halogenated paraffin, polybiphenyl chloride, dimethylnaphthalene and dibutyl phthalate.

In the above described photoconductors according to the present invention, if necessary, an adhesive or barrier layer can be interposed between the electroconductive support and the photoconductive layer. The adhesive layer or the barrier layer can be made of, for example, polyamide, nitrocellulose, or aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charge photoconductor is exposed to a light image so that a latent electrostatic image is formed on the photoconductor. The thus formed latent electrostatic image is developed by a developer to a visible image, and, when necessary, the developed image can be transferred to a sheet of paper. The photoconductors according to the present invention have high photosensitivity and excellent flexibility.

Other features of this invention will become apparent in the course of the following description of exemplary embodiments, which are given for illustration of the invention and are not intended to be limiting thereof.

EXAMPLE 1

The following components were ground and dispersed in a ball mill to prepare a charge generation layer coating liquid:

| | Parts by Weight |
|---|---|
| Diane Blue (C.I. Pigment Blue 25, C.I. 21180) (Charge generating material of the formula in Table 3) | 76 |
| 2% Tetrahydrofuran solution of a polyester resin (Trademark "Vylon 200" made by Toyobo Co., Ltd.) | 1,260 |
| Tetrahydrofuran | 3,700 |

This charge generation layer coating liquid was coated by a doctor blade on the aluminum-deposited surface of an aluminum-deposited polyester base film, which served as an electroconductive support, so that a charge generation layer was formed on the electroconductive support with a thickness of about 1 μm when dried at room temperature.

Then the following components were mixed and dissolved, so that a charge transport layer coating liquid was prepared:

| | Parts by Weight |
|---|---|
| 1,3-Pentadiene derivative No. 32 in Table 1 | 2 |
| Polycarbonate resin (Trademark "Panlite K 1300" made by Teijin Limited.) | 2 |
| Tetrahydrofuran | 16 |

The thus prepared charge transport layer coating liquid was coated on the aforementioned charge generation layer by a doctor blade and dried at 80° C. for 2 minutes and then at 105° C. for 5 minutes, so that a charge transport layer with a thickness of about 20 μm was formed on the charge generation layer. Thus, an electrophotographic photoconductor No. 1 according to the present invention was prepared.

EXAMPLES 2 TO 31

Example 1 was repeated except that the charge generating material and the 1,3-pentadiene derivative working as the charge transporting material employed in Example 1 were respectively replaced by the charge generating materials and the 1,3-pentadiene derivatives as listed in Table 3, whereby electrophotographic photoconductors No. 2 to No. 31 according to the present invention were prepared.

TABLE 3
| Photo-conductor No. | Charge Generating Material | Charge Transporting Material (1,3-pentadiene derivative No.) |
|---|---|---|
| 1 | 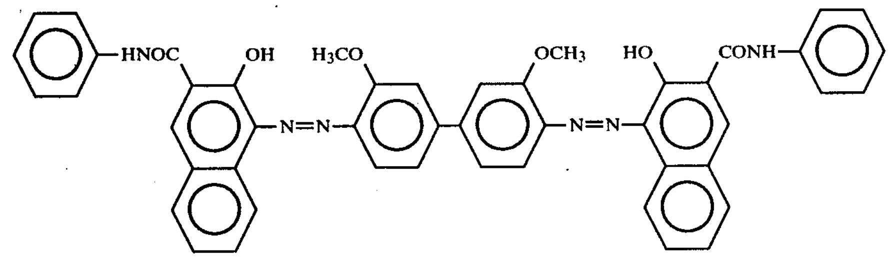 | 32 |
| 2 | 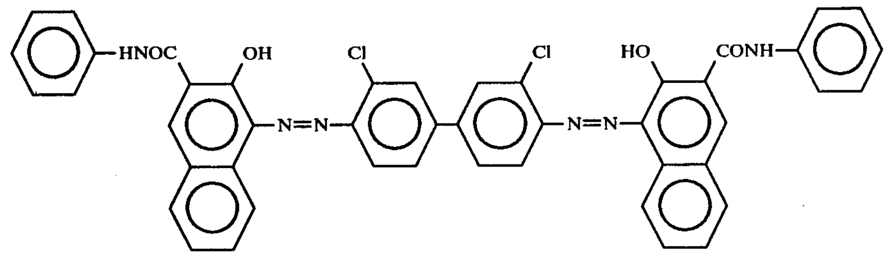 | 32 |
| 3 | 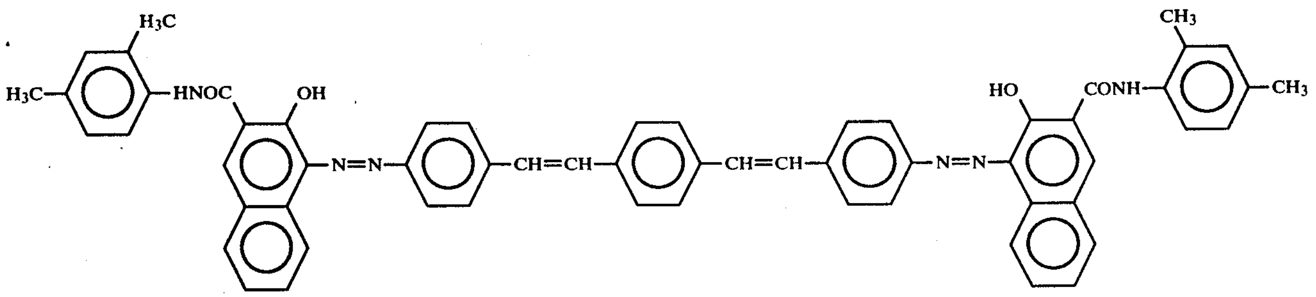 (thereinafter referred to as CG-1) | 32 |

TABLE 3-continued
| Photo-conductor No. | Charge Generating Material | Charge Transporting Material (1,3-pentadiene derivative No.) |
| --- | --- | --- |
| 4 | 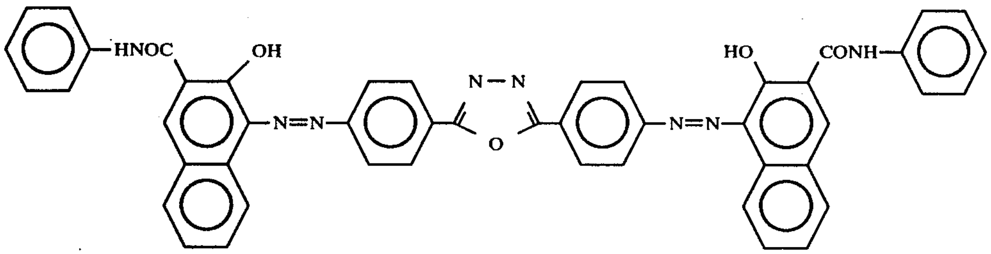 | 32 |
| 5 | 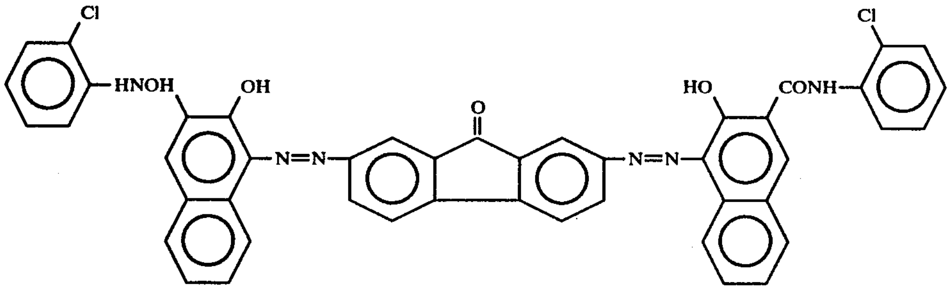 (thereinafter referred to as CG-1) | 32 |

TABLE 3-continued
| Photo-conductor No. | Charge Generating Material | Charge Transporting Material (1,3-pentadiene derivative No.) |
|---|---|---|
| 6 | 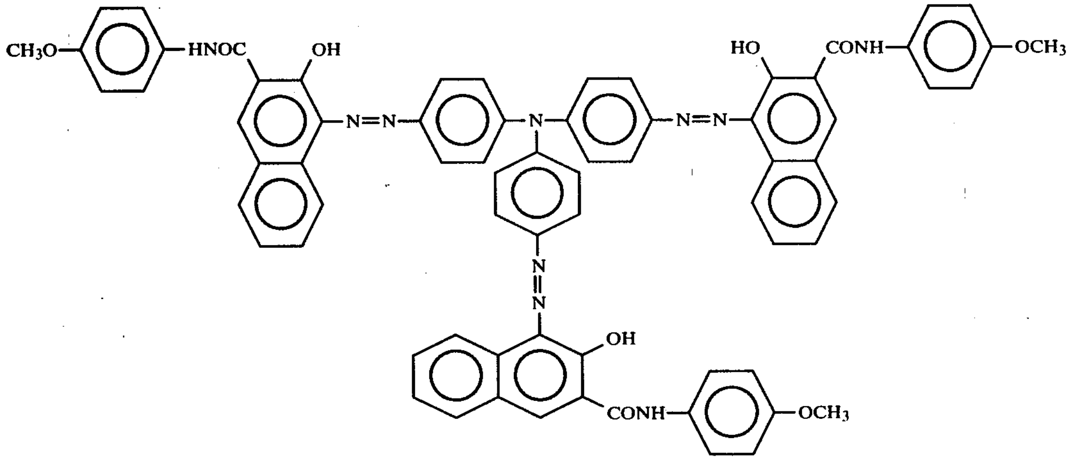 | 32 |
| 7 | β-type Copper Phthalocyanine | 32 |
| 8 | 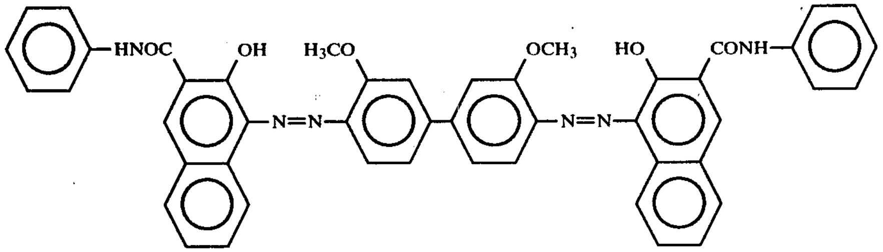 | 28 |

TABLE 3-continued
| Photo-conductor No. | Charge Generating Material | Charge Transporting Material (1,3-pentadiene derivative No.) |
|---|---|---|
| 9 | 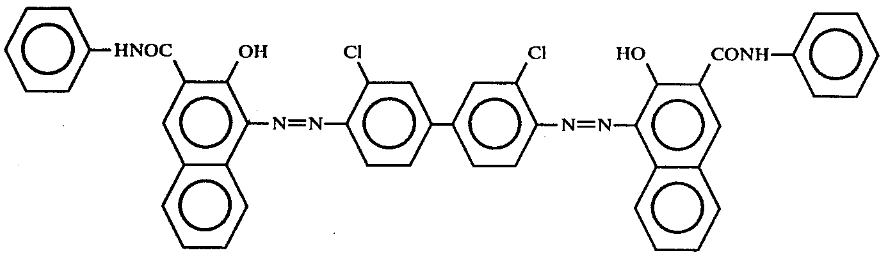 | 28 |
| 10 | CG-1 | 28 |
| 11 | CG-2 | 28 |
| 12 | CG-1 | 2 |
| 13 | CG-2 | 2 |
| 14 | CG-1 | 58 |
| 15 | CG-2 | 58 |
| 16 | CG-1 | 13 |
| 17 | CG-2 | 13 |
| 18 | CG-1 | 33 |
| 19 | CG-2 | 33 |
| 20 | CG-1 | 34 |
| 21 | CG-2 | 34 |
| 22 | CG-1 | 35 |
| 23 | CG-2 | 35 |
| 24 | CG-1 | 44 |
| 25 | CG-2 | 44 |
| 26 | CG-1 | 61 |
| 27 | CG-2 | 61 |
| 28 | CG-1 | 58 |
| 29 | CG-2 | 58 |
| 30 | CG-1 | 23 |
| 31 | CG-2 | 23 |
| 32 | CG-1 | 20 |
| 33 | CG-2 | 20 |

EXAMPLE 34

Selenium was vacuum-deposited with a thickness of about 1.0 μm on an about 300 μm thick aluminum plate so that a charge generation layer was formed on the aluminum plate.

A charge transport layer coating liquid was prepared by mixing and dispersing the following components:

| | Parts by Weight |
|---|---|
| 1,3-Pentadiene derivative No. 32 in Table 1 | 2 |
| Polyester resin (Trademark "Polyester Adhesive 49000" made by Du Pont Co.) Limited.) | 3 |
| Tetrahydrofuran | 45 |

The thus prepared charge transport layer coating liquid was coated on the above-prepared selenium-deposited charge generation layer by a doctor blade, dried at room temperature and further dried under reduced pressure, so that a charge transport layer with a thickness of about 10 μm was formed on the charge generation layer. Thus an electrophotographic photoconductor No. 34 according to the present invention was prepared.

EXAMPLE 35

Example 34 was repeated except that selenium-deposited charge generation layer with a thickness of about 1.0 μm was replaced by a charge generation layer comprising a perylene pigment having the following formula with a thickness of about 0.6 μm, whereby an electrophotographic photoconductor No. 35 was prepared.

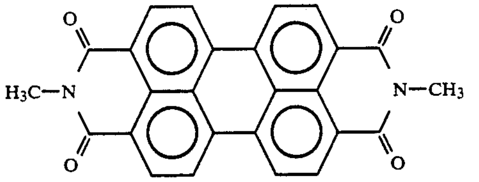

EXAMPLE 36

A mixture of 1 part by weight Diane Blue (the same as employed in Example 1) and 158 parts by weight of tetrahydrofuran was ground and dispersed in a ball mill. To this mixture, 12 parts by weight of the 1,3-pentadiene derivative No. 32 and 18 parts by weight of a polyester resin (Trademark "Polyester Adhesive 49000" made by Du Pont Co.) were added and mixed, whereby a photoconductive layer coating liquid was prepared.

The thus prepared photoconductive layer coating liquid was coated on an aluminum-deposited polyester film by a doctor blade and dried at 100° C. for 30 minutes, so that a photoconductive layer with a thickness of about 16 μm was formed on the aluminum-deposited polyester film. Thus an electrophotographic photoconductor No. 36 according to the present invention was prepared.

EXAMPLE 37

The same charge transport layer coating liquid as that prepared in Example 1 was coated by a doctor blade on the aluminum-deposited surface of an aluminum-deposited polyester base film, which served as an electroconductive support, so that a charge transport layer was formed on the electroconductive support, with a thickness of about 20 μm when dried at room temperature.

Then the following components were ground and dispersed in a ball mill to prepare a dispersion:

| | Parts by Weight |
|---|---|
| Bisazo pigment (a charge generation pigment "CG-2" shown in Table 3) | 13.5 |
| Polyvinyl butyral (Trademark "XYHL" made by Union Carbide Plastic Co., Ltd.) | 5.4 |
| Tetrahydrofuran | 680 |
| Ethyl cellosolve | 1020 |

To the above dispersion, 1700 parts by weight of ethyl cellosolve were further added and the mixture was dispersed, whereby a charge generation layer coating liquid was prepared.

The thus prepared charge generation layer coating liquid was coated on the aforementioned charge transport layer by spray coating and dried at 100° C. for 10 minutes, whereby a charge generation layer having a thickness of about 0.2 μm was formed on the charge transport layer.

Then a methanol/n-buthanol solution of a polyamide resin (Trademark "CM-8000" made by Toray Industries, Inc.) was coated on the charge generation layer by spray coating and dried at 120° C. for 30 minutes, whereby a protective layer having a thickness of about 0.5 μm was formed on the charge generation layer. Thus an electrophotographic photoconductor No. 37 according to the present invention was prepared.

The thus prepared electrophotographic photoconductors No. 1 to No. 37 according to the present invention were charged negatively or positively in the dark under application of −6 kV or +6 kV of corona charge for 20 seconds and then allowed to stand in the dark for 20 seconds without applying any charge thereto. At this moment, the surface potential $V_{po}$ (V) of each photoconductor was measured by a Paper Analyzer (Kawaguchi Electro Works, Model SP-428). Each photoconductor was then illuminated by a tungsten lamp in such a manner that the illuminance on the illuminated surface of the photoconductor was 4.5 lux, so that the exposure $E_{1/2}$ (lux·seconds) required to reduce the initial surface potential $V_{po}$ (V) to ½ the initial surface potential $V_{po}$ (V) was measured. The results are shown in Table 4.

TABLE 4

| Ex. No. | 1,3-pentadiene Derivative No. | $V_{po}$ (V) | $E_{1/2}$ (lux sec) |
|---|---|---|---|
| 1 | 32 | −1110 | 1.01 |
| 2 | 32 | −990 | 1.20 |
| 3 | 32 | −1220 | 1.40 |
| 4 | 32 | −1130 | 1.25 |
| 5 | 32 | −1036 | 1.02 |
| 6 | 32 | −1210 | 1.00 |
| 7 | 32 | −975 | 1.05 |
| 8 | 28 | −1300 | 1.43 |
| 9 | 28 | −1205 | 1.20 |
| 10 | 28 | −1163 | 1.47 |
| 11 | 28 | −1083 | 1.24 |
| 12 | 2 | −1270 | 1.70 |
| 13 | 2 | −1220 | 1.43 |
| 14 | 58 | −1160 | 1.30 |
| 15 | 58 | −1005 | 0.99 |
| 16 | 13 | −1120 | 1.90 |
| 17 | 13 | −1030 | 1.41 |
| 18 | 33 | −1200 | 1.12 |

TABLE 4-continued

| Ex. No. | 1,3-pentadiene Derivative No. | $V_{po}$ (V) | $E_{\frac{1}{2}}$ (lux sec) |
|---|---|---|---|
| 19 | 33 | −1110 | 0.98 |
| 20 | 34 | −1120 | 1.20 |
| 21 | 34 | −975 | 0.97 |
| 22 | 35 | −1040 | 1.05 |
| 23 | 35 | −925 | 0.95 |
| 24 | 44 | −1130 | 1.03 |
| 25 | 44 | −1025 | 0.89 |
| 26 | 61 | −1120 | 0.92 |
| 27 | 61 | −1030 | 0.70 |
| 28 | 58 | −1160 | 1.30 |
| 29 | 58 | −1005 | 0.99 |
| 30 | 23 | −1290 | 2.71 |
| 31 | 23 | −1260 | 2.22 |
| 32 | 20 | −1420 | 1.80 |
| 33 | 20 | −1354 | 1.90 |
| 34 | 32 | −850 | 3.01 |
| 35 | 32 | −1270 | 3.20 |
| 36 | 32 | +1350 | 1.20 |
| 37 | 32 | +950 | 0.90 |

Each of the above electrophotographic photoconductors No. 1 through No. 37 was incorporated in a commercially available electrophotographic copying machine and a latent electrostatic image was formed thereon by being exposed to light image. The latent electrostatic image was developed with a dry-type developer to a visible toner image, electrostatically transferred to a transfer sheet made of plain paper and fixed thereto. As a result, a clear transferred image was obtained by each of the photoconductors. When a liquid developer was employed instead of the dry-type developer, clear transfer images were obtained likewise.

According to the present invention, not only the photoconductive properties, but also resistance to thermal and mechanical shock of the electrophotographic photoconductors comprising an electroconductive support and a photoconductive layer formed thereon which comprises at least one of the 1,3-pentadiene derivatives having the formula (I) in which $R^1$ and $R^2$ may be a methyl group at the same time are superior to those of conventional photoconductors. Furthermore, the manufacturing cost of the above electrophotographic photoconductors according to the present invention is low.

What is claimed is:

1. A 1,3-pentadiene derivative having formula (I):

$$A—CH{=}CH—CH{=}CH—CH_2—A \qquad (I)$$

wherein: A represents

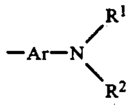

in which Ar represents (a) a phenylene group which may be substituted with a substituent selected from the group consisting of an alkyl group having 1 to 4 carbon atoms and an alkoxy group having 1 to 4 carbon atoms; (b) a biphenylene group; or (c) a naphthylene group which may be substituted with a substituent selected from the group consisting of an alkyl group having 1 to 4 carbon atoms and an alkoxy group having 1 to 4 carbon atoms; $R^1$ and $R^2$ each represent (i) an alkyl group having 1 to 4 carbon atoms substituted with a phenyl group which may be substituted with an alkyl group having 1 to 4 carbon atoms or an alkoxyl group having 1 to 4 carbon atoms or (ii) a phenyl group which may be substituted with a substituent selected from the group consisting of an alkyl group having 1 to 4 carbon atoms, an alkoxy group having 1 to 4 carbon atoms, a halogen atom, and a phenyl group.

2. The 1,3-pentadiene derivative of claim 1, wherein at least one of $R^1$ and $R^2$ is phenylmethyl or phenyl.

3. The 1,3-pentadiene derivative of claim 1, wherein Ar is naphthylene.

4. The 1,3-pentadiene derivative of claim 1, wherein Ar is phenylene.

* * * * *

UNITED STATES PATENT AND TRADEMARK OFFICE

CERTIFICATE OF CORRECTION

PATENT NO. : 5,166,438

DATED : November 24, 1992

INVENTOR(S) : Hashimoto et al.

It is certified that error appears in the above-identified patent and that said Letters Patent is hereby corrected as shown below:

Column 1, line 68, "9-on U.S." should read --9-on (U.S. --.

Column 2, line 12, "have many" should read --are--.

Column 5, line 5, "formula I)" should read --formula (I) --.

Column 23, line 20, "us" should read --use--.

Column 26, line 42, "above mentioned" should read --above-mentioned--.

Column 26, line 49, "above described" should read --above-described--.

Signed and Sealed this

Eighteenth Day of January, 1994

*Attest:*

BRUCE LEHMAN

*Attesting Officer* — *Commissioner of Patents and Trademarks*